United States Patent
Matsumoto et al.

(10) Patent No.: US 8,076,460 B2
(45) Date of Patent: Dec. 13, 2011

(54) ANTIBODY AND INHIBITOR, AND TRANSFECTION METHOD OR KIT USING THEM

(75) Inventors: Misako Matsumoto, Ikoma (JP); Tsukasa Seya, Nara (JP)

(73) Assignee: Japan Science and Technology Agency, Saitama (JP)

( * ) Notice: Subject to any disclaimer, the term of this patent is extended or adjusted under 35 U.S.C. 154(b) by 411 days.

(21) Appl. No.: 12/314,556

(22) Filed: Dec. 12, 2008

(65) Prior Publication Data

US 2009/0105460 A1    Apr. 23, 2009

Related U.S. Application Data

(63) Continuation of application No. 10/512,873, filed as application No. PCT/JP03/01673 on Feb. 17, 2003, now abandoned.

(30) Foreign Application Priority Data

Jun. 12, 2002   (JP) ................................ 2002-171952

(51) Int. Cl.
*C07K 16/00*    (2006.01)
(52) U.S. Cl. .................... 530/388.1; 530/387.1
(58) Field of Classification Search .......... None
See application file for complete search history.

(56) References Cited

U.S. PATENT DOCUMENTS

| | | | |
|---|---|---|---|
| 7,271,248 | B2 | 9/2007 | Hardiman et al. |
| 2003/0032090 | A1 | 2/2003 | Hardiman et al. |

FOREIGN PATENT DOCUMENTS

| | | |
|---|---|---|
| JP | 2000-109435 | 4/2000 |
| JP | 2002-514083 | 5/2002 |
| JP | 2002-171952 | 6/2002 |
| WO | 98/22605 | 5/1998 |
| WO | 98/50547 | 11/1998 |
| WO | WO9850547 | * 11/1998 |
| WO | 99/38008 | 7/1999 |
| WO | 00/18437 | 4/2000 |

OTHER PUBLICATIONS

Sarkar et al (JBC 278:4393-4396, online published Dec. 30, 2002.*
Cario et al Infec. &Immun. 68: 7010-17, Dec. 2000.*
Matsumoto et al BBRC 293:1364-1369, May 2002, IDS, filed Jan. 6, 2009, item: QR.*
Alexopoulou et al. Recognition of double-stranded RNA and activation of NF-κB by Toll-like receptor 3, Nature 413:732-738 (Oct. 2001).
Kurata et al. "Differential expression of granulocyte-macrophage colony-stimulating factor and IL-3 receptor subunits on human CD34+ cells and leukemic cell lines" J. Allergy Clin. Immunol. 96:1083-1099 (Dec. 1995).
Matsumoto & Seya "Recognition of dsRNA by Toll-like receptor 3" Uirusu (Virus) 51:209-214 (Dec. 2001).
Matsumoto & Seya "Functional analysis of Toll-like receptor 3" Abstract 0879, 3-B-W17-16-O/P, The 31st Annual Meeting of the Japanese Society of Immunology, Proceedings 31:232 (Dec. 2001).
Matsumoto et al. "Establishment of a monoclonal antibody against human Toll-like receptor 3 that blocks double-stranded RNA-mediated signaling" Biochem. Biophys. Res. Comm. 293:1364-1369 (May 2002).
Matsumoto et al. "Subcellular localization of Toll-like receptor 3 in human dendritic cells" J. Immunol. 171:3154-3162 (Sep. 2003).
Price "Production and characterization of synthetic peptide-derived antibodies" in Ritter & Ladyman (eds.) *Monoclonal Antibodies*, Cambridge University Press, pp. 60-84 (1995).
International Search Report for PCT/JP2003/001673 dated Apr. 15, 2003.
Tachibana "A method of producing monoclonal antibodies rapidly and highly efficiently by using iliac lymph nodes of rat" Forum on Biomolecular Chemistry 21:25-28 and downloaded from http://www.chem.eng.osaka-u.ac.jp/FBC/FBCmember/FBC_NewsLetterNo21.pdf (Jun. 2006).
Ukai et al., Japanese Trial Decision for related Appln. No. JP 2002-171952, eight pages, and English translation thereof (Mar. 2009).

* cited by examiner

*Primary Examiner* — Misook Yu
*Assistant Examiner* — Lei Yao
(74) *Attorney, Agent, or Firm* — Nixon & Vanderhye P.C.

(57) ABSTRACT

The present invention provides a monoclonal antibody which specifically binds to human Toll-like receptor 3 and inhibits production of type 1 interferon. It also provides an inhibitor which (a) suppresses a double-stranded RNA-mediated immune response in a cell which expresses Toll-like receptor 3 that recognizes the double-stranded RNA and produces type I interferon, and (b) includes an antibody, which binds to the Toll-like receptor 3 and inhibits production of the type I interferon. Particularly, the monoclonal antibody is against human Toll-like receptor 3. Further, a transfection method and kit are provided. Production of type I interferon can be controlled by using an antibody which specifically binds to Toll-like receptor 3 that recognizes a double-stranded RNA and produces type I interferon.

1 Claim, 4 Drawing Sheets

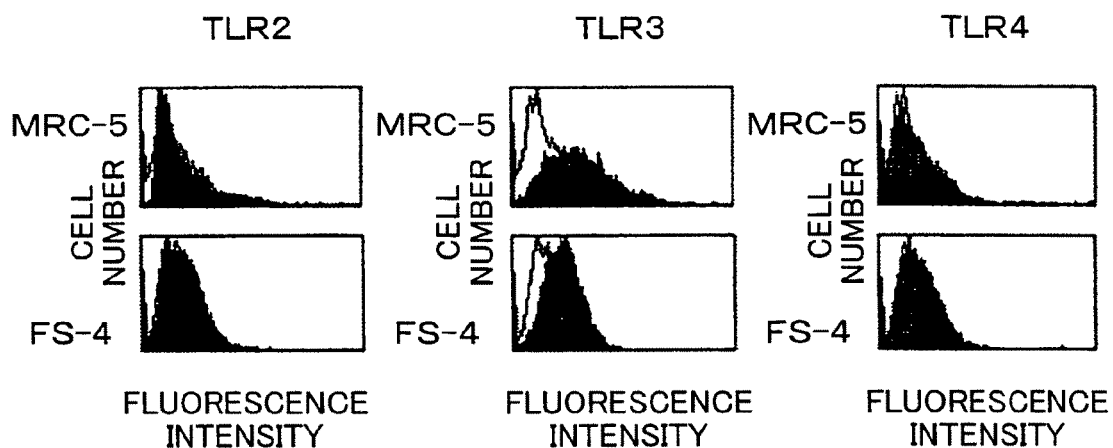
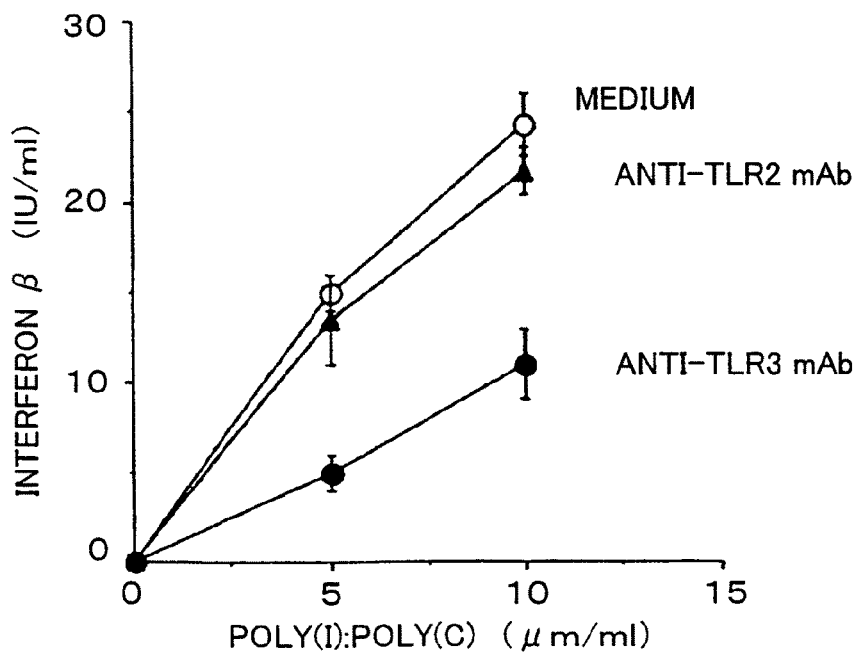

ANTIBODY AND INHIBITOR, AND TRANSFECTION METHOD OR KIT USING THEM

This application is a continuation of application Ser. No. 10/512,873, filed Oct. 29, 2004, now abandoned; which is a U.S. national stage under 35 U.S.C. 371 of Appln. No. PCT/JP2003/001673 filed Feb. 17, 2003.

TECHNICAL FIELD

The present invention relates to (i) an antibody specifically bound to human Toll-like receptor 3, (ii) an inhibitor for blocking a signaling induced by double-stranded RNA (ribonucleic acid) so as to suppress a double-stranded RNA-mediated immune response in a cell which produces type I interferon (interferon-α and interferon-β) by expressing the Toll-like receptor recognizing the double-stranded RNA on the surface, (iii) a transfection method or a transfection kit using the antibody and the inhibitor so as to carry out transfection with a recombined RNA virus vector in which a gene of interest is inserted.

BACKGROUND ART

It is said that there have been viruses since so early stage of birth of life and have been evolving while contributing to evolution of organisms. There are many viruses having RNA as a gene (RNA viruses), and 90% of plant viruses are RNA viruses.

Recently, a method for introducing genetically-engineered genes into mammalian cells (a transfection method for animal cells) has been being studied intensively. As the method for introducing genes, a method utilizing a virus (such as a retrovirus) as a vector (a virus vector) (called a virus method) in order to transfect animal cells is widely used due to its relatively high transfection efficiency. In such a method utilizing a virus vector, a host cell is infected with the virus vector (a recombinant virus), thereby introducing a gene of interest into the host cell, wherein the virus vector is produced by partially recombining the gene of the virus with the gene of interest to be introduced or a promoter which can function in the host cell, or the like. Thus, the host cell uptakes and expresses an exogenous gene (i.e. a foreign gene).

In the virus method, it is necessary to use a virus vector having a high infection efficiency in order to obtain a sufficient transfection efficiency. The infection efficiency depends on many factors in a virus and/or a host cell such as: an invasion efficiency of the virus into the cell; a replication efficiency of the virus in the cell (some cells cannot be used for some viruses: this replication efficiency is referred to also as tropism); an expression efficiency of the viral gene in the host cell (an incorporation property into a genome, the number of viral gene copies, and the like); and the like. In order to improve the infection efficiency, various measures such as selection of cell types, improvement of a vector, addition of a secondary factor such as a T-antigen, and the like have been devised. However, the improvement of the infection efficiency has not yet been achieved, and is the largest factor which prevents application of the virus vector as a multipurpose vector. When a highly infectious virus vector is used, the gene recombinant is more likely to leak to the outside of an experimental laboratory so as to affect the environment.

Thus, there is great need for a technique for improving the transfection efficiency by treating the host cell as necessary without enhancing the infectious capacity of the virus vector itself. Each of cells of plants, insects, invertebrates, and vertebrates has an immune system for suppressing infection of an RNA virus as a host defense mechanism of organisms (a bioregulation mechanism). Thus, when it is possible to artificially depress the immune function, it may be possible to further improve the transfection efficiency in the virus method.

Recently, it is a problem to resolve the mechanism of the immune system how an innate immunity (basic immunity) system of plant, insects, invertebrates, and vertebrates detects and prevents virus invasion. A bioregulation mechanism (such as production of antibodies, and onset against virus-infected cells by lymph cells (called cytotoxic T lymph cells (CTLs)) has been developed by an acquired immune system appeared in the vertebrates. However, in order that the bioregulation mechanism functions sufficiently, it is necessary to help of the innate immunity such as an antigen-presenting cell. With completion of Genome Projects in various organisms, molecules involved in the innate immunity systems critical to the host defense (infection control) mechanism against bacteria and viruses are being identified. It has not been clarified for a long time which molecule regulates the host defense mechanism against the viral infection according to the innate immunity system and how to regulate the host defense mechanism by the molecule in human. However, only recently, it is gradually clarified to analyze the host defense mechanism at molecular level.

An initial immune response against a virus or a bacteria has been conventionally considered to be non-specific. However, a receptor group called microbial receptors was identified, so that it was clarified that: an immunocompetent cell of the innate immunity system such as macrophage and a dendritic cell detects foreign substances entered via a receptor, induces release of cytokine and activates lymph cells by expression of sub-stimulating molecules.

A Toll-like receptor which recognizes various microbial components and transmits a danger signal into a host is one of the foregoing microbial receptors, and such Toll-like receptors exist in plants, insects, mammals, and the like regardless of kinds. The Toll-like receptor is a homologue of a membrane protein (Drosophia Toll) involved in both development and immunity of *Drosophila*. Eleven members of the Toll-like receptors are found in human, and twelve members of the Toll-like receptors are found in mice. These Toll-like receptors constitute a group of a receptor family called a Toll-like receptor family. The Toll-like receptor has been noticed as a microbial receptor recently, and it has been clarified that the Toll-like receptor is involved in recognition of various microbial components.

Further, recently, it has been clarified that: a Toll-like receptor 3 (TLR3) which is one (kind) of the Toll-like receptors recognizes double-stranded RNA so as to activate a nucleic factor κB (hereinafter, referred to as "NF-κB") (L. Alexopoulou, A. C. Holt, R. Medzhitov, R. A. Flavell, Nature 413 (2001) 732-738). That is, it was found that the Toll-like receptor 3 is a receptor involved in a double-stranded RNA-mediated signaling.

While, in the immune response of animal cells, it is known that type I interferon (interferon-α or interferon-β) which is one (kind) of cytokines plays an important role in defending against viral infection. Thus, it is considered that it is possible to drop an immune function against various kinds of viruses, when it is possible to prevent production of the type I interferon. Further, it is known that: when fibroblasts are stimulated with poly-(inosinic acid:cytidylic acid) (hereinafter, referred to as "poly(I):poly(C)" which is a synthesis analog of a viral double-stranded RNA (double-stranded RNA produced by a virus), transcription of the type I interferon is induced.

However, it has not been clarified how the animal cells recognize the viral double-stranded RNA and which signaling pathway produces the type I interferon. It was not known that signaling pathways involving in the production of the type I interferon exist in a downstream of the human Toll-like receptor 3.

DISCLOSURE OF INVENTION

The object of the present invention is to provide (i) an antibody against a Toll-like receptor having a function for inhibiting production of type I interferon which is induced by a viral double-stranded RNA, (ii) an inhibitor capable of suppressing immune response against a specific virus by inhibiting the production of the type I interferon induced by the viral double-stranded RNA, and (iii) a transfection method or a transfection kit by which it is possible to improve a transfection efficiency without enhancing an infection efficiency of a virus vector.

The inventors of the present invention created a monoclonal antibody (mAb) against the TLR3, and found that: signaling pathways involved in the production of the type I interferon exist in a downstream of the TLR3, and it is possible to block the signaling pathways by the monoclonal antibody (mAb) against the TLR3. That is, the inventors found that the monoclonal antibody against the TLR3 has a function for inhibiting the production of the type I interferon, thereby completing the present invention.

That is, the antibody according to the present invention is an antibody specifically bound to a human Toll-like receptor 3. Further, in order to achieve the foregoing object, the inhibitor according to the present invention is an inhibitor for suppressing a double-stranded RNA-mediated immune response in a cell which expresses a Toll-like receptor recognizing the double-stranded RNA and produces type I interferon, and the inhibitor comprises an antibody, preferably, a monoclonal antibody against the human TLR3, which binds to the Toll-like receptor and inhibits production of the type I interferon.

When the antibody or the inhibitor is used, the antibody binds to the Toll-like receptor recognizing the double-stranded RNA so that it is possible to inhibit the binding between the double-stranded RNA and the Toll-like receptor, thereby preventing the type I interferon from being produced in a downstream of signaling pathways involved in the immune response against the double-stranded RNA. Thus, the antibody suppresses the immune response in TLR3-expressing cells induced by the double-stranded RNA.

Thus, this antibody enables us to amplify RNA viral infection by suppressing the immune response. The suppression of the immune response is not observed in uninfected cells even in case of single-stranded RNA. However, the single-stranded RNA virus has a double-stranded RNA phase during a process of gene replication, so that it is possible to amplify (promote) single-stranded RNA viral infection. Thus, it is feasible to improve a transfection efficiency with a RNA virus vector such as a Sendai-virus vector, a retrovirus vector, and the like without enhancing an infectious efficiency of the virus vector. Note that, examples of the RNA virus include a negative-stranded RNA virus such as Sendai-virus, a positive-stranded RNA virus, and a double-stranded RNA virus. Each of these viruses replicates a large number of double-stranded RNAs in cells, so that infection of these viruses would be amplified by the antibody or the inhibitor.

Further, the antibody or the inhibitor can bind to the Toll-like receptor recognizing double-stranded RNA thereby suppressing the immune response in upstream of the signaling pathway, which leads to selective suppression of the immune response against the RNA virus. As a result, it is possible to maintain an immune function against antigens other than the RNA virus, e.g., a DNA (deoxyribo nucleic acid) virus, bacteria, and the like.

Further, in order to achieve the foregoing object, the transfection method according to the present invention comprises the step of infecting a cell which expresses a Toll-like receptor recognizing a double-stranded RNA and produces type I interferon with a recombined virus vector, in which a gene of interest has been inserted, under the inhibitory condition for production of the type I interferon by using the inhibitor of the present invention (which binds to the Toll-like receptor recognizing the double-stranded RNA and inhibits the production of the type I interferon).

Further, the transfection kit according to the present invention relates to a kit for transfecting a cell which expresses a Toll-like receptor recognizing a double-stranded RNA and produces type I interferon, and wherein the transfection kit comprises: an inhibitor including an antibody, which binds to the Toll-like receptor and inhibits production of the type I interferon; and a recombined RNA virus vector in which a gene of interest has been inserted.

According to them, as described above, it is possible to amplify (promote) infection of single-stranded RNA virus and double-stranded RNA virus with the inhibitor. Thus, it is possible to improve a transfection efficiency using RNA virus vector such as retrovirus vector without enhancing an infection efficiency of the virus vector.

Note that, in the present specification, the term "antibody or antibodies against . . . ," means "antibody or antibodies specifically bound to . . . ".

For a fuller understanding of the nature and advantages of the present invention, reference should be made to the ensuing detailed description taken in conjunction with the accompanying drawings.

BRIEF DESCRIPTION OF DRAWINGS

FIG. 1(a) shows a case using normal mouse cells as a control. FIG. 1(b) shows a case using mouse cells expressing TLR2. FIG. 1(c) shows a case using mouse cells expressing the TLR3.

FIG. 3(a), FIG. 3(b), and FIG. 3(c) are graphs each of which shows results of flow cytometric analysis in which two kinds of human fibroblasts are analyzed by using monoclonal antibodies against various kinds of TLRs. FIG. 3(a) shows a case using a monoclonal antibody against human TLR2. FIG. 3 (b) shows a case using a monoclonal antibody against human TLR3. FIG. 3(c) shows a case using a monoclonal antibody against human TLR4.

FIG. 4 is a graph showing a result obtained by measuring concentrations of interferon-β when human lung fibroblasts pretreated with the anti-TLR2 monoclonal antibody or the anti-TLR3 monoclonal antibody is stimulated with poly(I):poly(c).

BEST MODE FOR CARRYING OUT THE INVENTION

Figure 1:
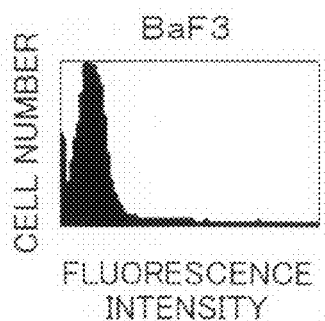
FIG. 1(a), FIG. 1(b), and FIG. 1(c) are graphs each of which shows a result of flow cytometric analysis in which mouse cells is analyzed by using a monoclonal antibody against the TLR3.
Figure 1:
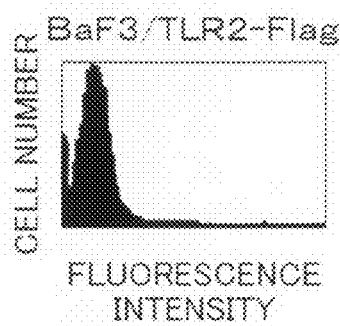
Figure 1:
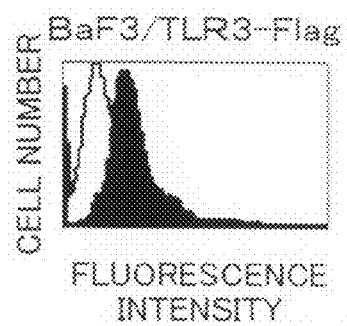

First, the inventors of the present invention confirmed that: human fibroblasts selectively express TLR3 on their cell surface, and type I interferon, particularly interferon-β, is produced upon viral infection or treatment with poly(I):poly(c) which is double-stranded RNA. Next, the inventors generated a monoclonal antibody against human TLR3 in order to identify the function of TLR3 and the ligands for TLR3. Then, production of interferon-β by poly(I):poly(c) was suppressed by the monoclonal antibody against human TLR3. Thus, it was found that human TLR3 is a receptor for the double-stranded RNA produced by an RNA virus.

By the foregoing study, the inventors obtained such novel and original finding that "double-stranded RNA-mediated interferon-β production can be interrupted by binding the monoclonal antibody against the human TLR3, and the monoclonal antibody partially inhibits the double-stranded RNA-mediated cellular responses".

The present invention was completed on the basis of the foregoing finding. The inhibitor according to the present invention is an inhibitor for suppressing a double-stranded RNA-mediated immune response (particularly, immune response to viral infection) in a cell which expresses a Toll-like receptor (particularly, human Toll-like receptor 3) recognizing the double-stranded RNA and produces type I interferon (particularly, interferon-β), and wherein the inhibitor comprises an antibody (particularly, a monoclonal antibody against human Toll-like receptor 3), which binds to the Toll-like receptor and inhibits production of the type I interferon.

First, the Toll-like receptor is described as follows.

Mammalian Toll-like receptors (hereinafter, referred to as TLRs as required) recognize a variety of microbial nucleic acid-derivatives, metabolites, and products to induce activation of NF-κB and other signaling pathways. Ten members of the TLR family have been so far identified in humans, and are called human TLR1 through human TLR10.

Each TLR protein comprises an extracellular domain containing leucine-rich repeats (LRRs) domains, a C-terminal flanking region (LRRCT), and an intercellular domain containing a cytoplasmic signaling domain, that is, a so-called Toll/interleukin-1 receptor homology domain (Toll/IL-1R domain: TIR domain) (see L. A. O'Neil and C. A. Dinarello, Immunol. Today 21 (2000) 206-209). A typical LRR has a repeat structure consisting of 24 amino acids containing conserved asparagine residual groups and leucine residual groups, and is included in various proteins of bacteria, yeasts, plants, and animals, so that LRR domain is considered to act upon protein-protein interaction.

The ligands namely pathogen-associated molecular pattern (PAMP) and their elicited immune responses, though all are not clearly identified yet, differ among the TLRs.

As the TLR recognizing the double-stranded RNA, human TLR3 and mouse TLR3 were identified. It has been confirmed that the TLR3 recognizes double-stranded RNA by the study using a TLR3-knock-out mouse of the aforementioned document (L. Alexopoulou, A. C. Holt, R. Medzhitov, R. A. Flavell, Nature 413 (2001) 732-738) and the study (described later) performed by the inventors of the present invention.

The human TLR3 is an I-type membrane protein consisting of 904 amino acids. The extracellular LRR domain of the TLR3 comprises 23 LRRs whose motifs are conserved in more preferable manner than those of other TLRs. The intercellular TIR domain of the TLR3 is slightly different from that of other TLR in that amino acids in a conserved region essential for the receptor signaling are different. The TLR3 gene exists in a long arm q35 of chromosome IV. Further, in terms of a genome structure, although other TLRs are encoded by one or two exons, an open reading frame (ORF) of the TLR3 is encoded by four exons. Further, only the TIR domain of the TLR3 is split into two exons.

As cells according to the present invention, any cells can be used as long as the cells express TLR recognizing a viral double-stranded RNA and produce the type I interferon. It is preferable to use cells which express TLR recognizing the viral double-stranded RNA on their surface and produce the type I interferon when recognizing the double-stranded RNA.

According to the study performed by the inventors of the present invention, the human TLR3 is expressed in various dendritic cell (DC) subsets. Further, it has been reported that the human TLR3 is expressed in human intestinal epithelial cells (M. Muzio, D. Bosisio, N. Polentarutti, G. D'amico, A. Stoppacciro, R. Mancinelli C. van'tVeer, G. Penton-Rol, L. P. Ruco, P. Allavena, and A. Mantovani: J. Immunol. 164 (2000) 5998-6004, and E. Cario and D. K. Podolsky: Infect. Immun. 68 (2000) 7010-7017). These facts suggest that the function of the human TLR3 is closely connected with responses to microbial nuclear products in the innate immune system. Thus, the present invention is effective with respect to cells which express the human TLR3 and produce the type I interferon, particularly, cells which express the human TLR3 on their surface and produce interferon-β when recognizing an RNA virus. Examples of such cells include: human fibroblasts such as human lung fibroblasts, human foreskin fibroblasts, and the like; human dendritic cells; human intestinal epithelial cells; and the like. Particularly, fibroblasts are known to produce interferon-β upon viral infection or treatment with double-stranded RNA through different signaling pathways, so that its effect is expected to be great. Further, examples of the cells which express the mouse TLR3 so as to produce the interferon-β include mouse fibroblasts and the like.

In the human fibroblasts, the interferon-β is produced merely by adding poly(I):poly(C) to the cells. However, in mouse embryonic fibroblasts, DEAE-dextran is essential to producing interferon-β in addition to the stimulation with poly(I):poly(C) in general. This suggests a possibility that the human fibroblasts and the mouse fibroblasts are different from each other in terms of localization of the expressed receptor protein and a possibility that they are different from each other in terms of mechanisms of interferon-β production by poly(I):poly(C). Thus, it can be considered that the inhibitor according to the present invention can inhibit the interferon-β production more effectively in the cells which express the human TLR3 on their cell surface than in the cells which express the mouse TLR3.

Next, the antibody bound to TLR is described as follows.

As the antibody according to the present invention, any antibody can be used as long as the antibody can be bound to TLR, and a polyclonal antibody against TLR etc. may be used. It is preferable to use a monoclonal antibody against TLR, particularly, a monoclonal antibody against the human TLR3 because of the following reasons: properties of the monoclonal antibody are homogenous; it is easy to supply the monoclonal antibody; the monoclonal antibody can be varied into a human antibody in the future; the monoclonal antibody can be semi-permanently stored as the state of hybridoma; and the like. By using such a monoclonal antibody against TLR3, it is possible to effectively suppress the type I interferon production elicited by the double-stranded RNA.

The monoclonal antibody is generated by the following method. First, TLR protein, fragments, or other derivatives, or analogs thereof, or cells expressing them are used as an immunogen so as to immunize mouse splenetic lymph cells, and the immunized mouse splenetic lymph cells are fused with mouse myeloma cells so as to produce hybridoma. Next, the monoclonal antibody can be produced by the hybridoma. Various methods for immunization known in the art can be used for the present invention: for example, a hybridoma method (Kohler, G. and Milstein, C., Nature 256, 495-497 (1975)), a trioma method, human B-cells hybridoma method (Kozbor, Immunology Today 4, 72 (1983)), and EBV-hybridoma method (Monoclonal Antibodies and Cancer Therapy, Alan R Liss, Inc., 77-96 (1985)).

Note that, the inhibitor according to the present invention may include not only the antibody but also other component which does not interrupt a function of the antibody.

Next, transfection using the inhibitor according to the present invention is described as follows.

The transfection method according to the present invention relates to an infection method comprising subjecting a recombined RNA virus vector, in which a gene of interest has been inserted, to cells (particularly, human fibroblasts) which express TLR (particularly, human TLR3) recognizing the double-stranded RNA and produce the type I interferon (particularly, interferon-β), under the inhibitory condition for production of the type I interferon by using the inhibitor according to the present invention.

Further, the transfection kit according to the present invention is a kit for transfecting cells which express TLR recognizing the double-stranded RNA and produce the type I interferon, and comprises the inhibitor according to the present invention and a recombined RNA virus vector in which a gene of interest has been inserted.

The target cells are not particularly limited as long as the cells express TLR recognizing the double-stranded RNA and produce the type I interferon, and a foreign gene can be introduced into the cells by the RNA virus vector. However, in case where the inhibitor used comprises the monoclonal antibody against the human TLR3, it is preferable to use the cells which express the human TLR3, and it is more preferable to use cells which express the human TLR3 on their cell surface, for example, human fibroblasts, human dendritic cells, human intestinal epithelial cells, and the like. Further, it is considered that a useful transfectant can be obtained when human stem cells are used as target cells.

As the recombined RNA virus vector, any virus vector can be used as long as the virus vector is prepared by inserting a foreign gene (a gene of interest) into the virus gene of the virus vector having RNA as a gene. A method for inserting the foreign gene into the virus gene is not particularly limited, and various known methods can be used.

The RNA virus vector may be a virus vector having a single-stranded RNA as a gene (single-stranded RNA virus vector), or a virus vector having a double-stranded RNA as a gene (double-stranded RNA virus vector). Examples of the virus vector include Sendai virus vector, retrovirus vector, and the like. Among the foregoing virus vectors, a virus vector, such as Sendai virus vector, which produces a large amount of double-stranded RNAs, can be particularly effective in the present invention. Further, the retrovirus vector is preferable gene transfer means particularly in a gene therapy desired to express a gene for an extended period of time since the retrovirus vector is highly infectious, and enables the foreign gene to be introduced into cells with a high efficiency, and enables the foreign gene to be integrated into a chromosome DNA stably.

It is preferable to design the virus vector in various manners so as not to exert a bad influence to organisms in which the gene is introduced. For example, it is preferable that a virus vector used to introduce a gene replicates itself in cells and the replication function of the vector is defective so as to prevent infection (gene transfer) from being limitlessly repeated. Generally, it is possible to produce the replication-defective virus vector, in accordance with a method for preparing a virus vector packaged with viral particles by using virus producing cells (packaging cells).

In the transfection method according to the present invention, the method for inhibiting the type I interferon production in cells by using the inhibitor of the present invention is not particularly limited. For example, the inhibitor is added to cells cultured in a culture medium.

Further, in terms of inhibition of the type I interferon production, it is preferable to use the inhibitor of the present invention before infecting the cells with the recombined RNA virus vector in which the gene of interest has been inserted. The inhibitor and the recombined RNA vector may be used simultaneously. In case of using the inhibitor and the recombined RNA vector simultaneously, these are added to the cells cultured in the culture medium by mixture or separately.

Next, the present invention is further detailed on the basis of Examples, but the present invention is not limited to them.
[Cell Culture]

In the following Examples, normal human lung fibroblasts MRC-5 which had been obtained from Riken Cell Bank in Institute of Physical and Chemical Research (Tsukuba-shi Kouyadai 3-1-1, Ibaraki-ken Japan) was used as the human fibroblasts. Further, the normal human lung fibroblasts MRC-5 was maintained in MEM (Minimum Essential Medium: improved Eagle medium) supplemented with 10% heat-inactivated FCS (Fetal Calf Serum: product of JRH Biosciences) and antibiotics.

Further, human foreskin FS-4 fibroblasts (see J. Vilcek, M. Kohase, D. Henriksen-DeStefano, J. Cell. Physiol. 130 (1987) 37-43) and human embryonic kidney (HEK) 293 cells were maintained in DEM supplemented with 10% FCS and antibiotics.

Further, in the following Examples, interleukin 3 (IL-3) dependent murine cell line Ba/F3 was cultured in RPMI (Roswell Park Memorial Institute) culture medium containing 10% FCS, 5 ng/ml murine IL-3, 100 μM 2-mercaptoethanol (2-ME), and antibiotics.
[Reagent]

Poly(I):poly(C), polycytidylic acid (poly C), polyuridylic acid (poly U), and poly(dI):poly(dC) were purchased from Amersham Pharmacia Biotech. Polymyxin B, LPS from *Escherichia coli* serotype 0111:B4, and mouse IgG1 were from Sigma. The mycoplasma lipopeptide MALP-2 was prepared in accordance with a method recited by M. Nishiguchi, M. Matsumoto, T. Takao, M. Hoshino, Y. Shimonishi, S. Tsuji, N. A. Begum, O. Takuchi, S. Akira, K. Toyoshima, T. Seya: J. Immunol. 166 (2001) 2610-2616. Note that, the mycoplasma lipopeptide MALP-2 is lipopeptide consists of N-terminal fourteen amino acids of M161Ag.

These reagents, except for LPS, were treated with polymyxin B (10 μg/ml) for 1 h at 37° C. before stimulation of the cells.

[Monoclonal Antibody Against Human Toll-Like Receptor 4]

The monoclonal antibody against human TLR4 (HTA125) was a gift from Dr. Kensuke Miyake (Institute of Medical Science, University of Tokyo) (as to the production method thereof, see R. Shimazu, S. Akashi, H. Ogata, Y. Nagai, K. Fukudome, K. Miyake, M. Kimoto: J. Exp. Med. 189 (1999) 1777-1782).

[Complementary DNA Expression Vectors Encoding Human TLRs]

Complementary DNA expression vectors (pEFBOS expression vectors) encoding human TLR1, TLR2, and TLR3 were generated in accordance with the following method. First, a human monocyte was cultured in the presence of recombined human GM-CSF (granulocyte-macrophage colony stimulating factor) so as to obtain a complementary DNA (cDNA) library. Subsequently, the human TLR1, TLR2, and TLR3 were generated from the obtained cDNA library in accordance with PCR (polymerase chain reaction) method, and thus generated human TLR1, TLR2, and TLR3 were cloned in plasmid pEFBOS, so as to obtain three types of cDNA expression vectors, namely, pEFBOS expression vector encoding human TLR1 (human TLR1 expression vector), pEFBOS expression vector coding human TLR2 (human TLR2 expression vector), and pEFBOS expression vector coding human TLR3 (human TLR3 expression vector). Note that, plasmid pEFBOS was a gift from Dr. Shigekazu Nagata (Osaka University). The human TLR4 expression vector was a gift from Dr. Kensuke Miyake (Institute of Medical Science, University of Tokyo) (see R. Shimazu, S. Akashi, H. Ogata, Y. Nagai, K. Fukudome, K. Miyake, M. Kimoto: J. Exp. Med. 189 (1999) 1777-1782). These plasmids were prepared with a Plasmid Maxi kit (Qiagen).

[Stable Transfectants]

Murine cell Ba/F3 cells were transfected with pFEBOS expression vectors encoding human TLR2 or TLR3 together with pSV2neo plasmid (registered in RIKEN GenBank of Institute of Physical and Chemical Research) by electroporation so as to obtain a transfectant in which human TLR2 has been introduced or a transfectant in which human TLR3 has been introduced. The transfectants were selected with G418 for 10 days so as to obtain murine cells Ba/F3 stably expressing human TLR2 (stable transfectant) and murine cells Ba/F3 stably expressing human TLR3 (stable transfectant). Expression of each TLR was confirmed by intercellular staining for the flag epitope, which had been attached to the COOH-terminus of each TLR.

Example 1

In order to identify ligands for TLR3 by checking expression of TLR3 protein level and localization of TLR3 in terms of protein, the monoclonal antibody against human TLR3 was generated as the inhibitor according to the present invention.

That is, first, BALB/c mice were immunized with Ba/F3 cells stably expressing Flag-tagged (fluorescence-tagged) human TLR3, and then, spleen cells of the mice were fused with NS-1 myeloma cells so as to obtain an antibody producing hybridoma. From the antibody producing hybridoma, a monoclonal antibody against TLR3 was chosen by cell-surface staining of the same TLR3 transfectants used for immunization, so as to establish a monoclonal antibody against TLR3. The monoclonal antibody was named as TLR3.7. In the monoclonal antibody TLR3.7, immunoglobulin subclass was IgG1 and an L-chain was type κ. The hybridoma was deposited as FERM BP-10597 on Apr. 12, 2006 at the International Patent Organism Depositary (IPOD), National Institute of Advanced Industrial Science and Technology, Tsukuba Central 6, 1-1-1, Higashi, Tsukuba, Ibaraki, Japan.

Further, as a control, a monoclonal antibody against TLR2 was generated in the same manner as in the monoclonal antibody TLR3.7. The monoclonal antibody was named as TLR2.45. In the monoclonal antibody TLR2.45, immunoglobulin subclass was IgG1 and an L-chain was type κ.

Next, it was confirmed that the monoclonal antibody TLR3.7 recognized human TLR3 by using two assessment criteria in the supernatants of hybridomas.

As first assessment, the monoclonal antibody TLR3.7 was screened in accordance with flow cytometry.

The flow cytometry was performed as follows. The murine cells Ba/F3 stably expressing Flag-tagged (fluorescence-tagged) human TLR2 and TLR3 were incubated with the monoclonal antibody (1 μg) against TLR together with human IgG (10 μg) for 30 minutes at 4° C. in FACS (fluorescence activation cell sorter) buffer. Further, the FACS buffer is DPBS (Dulbecco's Phosphoric acid Buffer Solution) containing 0.5% BAS (Bovine Serum Albumin) and 0.1% sodium azide. After the cells were washed twice with the FACS buffer, FITC (fluorescence isothiocyanate)-labeled secondary antibody (American Qualex) was added and further incubated for 30 minutes at 4° C. The cells were then analyzed on a flow cytometer (FACS Calibur: product of Becton Dickinson).

Results of the flow cytometry are shown in FIG. 1(a), FIG. 1(b), and FIG. 1(c). Shaded histograms of FIG. 1(b) and FIG. 1(c) respectively show results obtained by staining the murine Ba/F3 cells, stably expressing Flag-tagged (fluorescence-tagged) human TLR2 and TLR3, with anti-TLR3 monoclonal antibody (TLR3.7) and FITC-labeled secondary antibody (American Qualex). Further, an open histogram of FIG. 1(c) represents cells labeled with an isotype-matched control antibody. Further, FIG. 1(a) shows a result obtained by staining the murine Ba/F3 cells (indicated by "BAF3" in FIG. 1(a), used as a control, with anti-TLR3 monoclonal antibody and the FITC-labeled secondary antibody.

As shown in FIG. 1(c), the peak of fluorescence of the murine Ba/F3 cells stably expressing the Flag-tagged human TLR3 (indicated by "BAF3/TLR3-Flag" in FIG. 1(c)) was shifted by the monoclonal antibody TLR3.7. Thus, the monoclonal antibody TLR3.7 was found to react with the murine Ba/F3 cells stably expressing the Flag-tagged human TLR3.

On the other hand, as shown in FIG. 1(b), the peak of fluorescence of the murine Ba/F3 cells stably expressing the Flag-tagged human TLR2 (indicated by "BAF3/TLR2-Flag" in FIG. 1(b)) was not shifted by the monoclonal antibody TLR3.7. Thus, the monoclonal antibody TLR3.7 was found not to react with the murine Ba/F3 cells stably expressing the human Flag-tagged TLR2.

Thus, in the transfection experiment, it was found that the monoclonal antibody TLR3.7 shows specificity to TLR3 and does not react with the murine Ba/F3 cells stably expressing TLR2.

Figure 2:
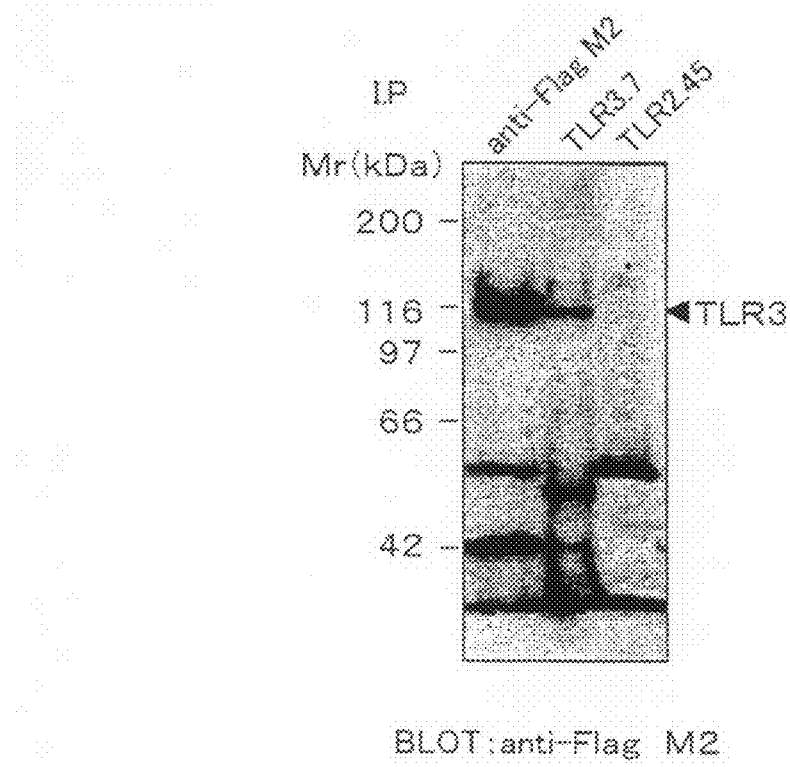
FIG. 2 shows a result obtained by immunoblotting the TLR3 that has been immunoprecipitated with an anti-Flag monoclonal antibody, an anti-TLR2 monoclonal antibody, or an anti-TLR3 monoclonal antibody.

As second assessment, a monoclonal antibody was chosen by immunoprecipitation using cell-lysates of the murine Ba/F3 cells expressing the Flag-tagged human TLR3. That is, immunoprecipitation with anti-flag antibody or anti-human TLR3 antibody was performed from the cell-lysates of transfectants as follows so as to judge expression of the Flag-tagged human TLR3 with anti-flag antibody. First, the murine Ba/F3 cells stably expressing the Flag-tagged human TLR2 was lysed using lysis buffer (Promega). Subsequently, TLR3 was immunoprecipitated with an anti-flag monoclonal antibody (M2: indicated by "anti-Flag M2" in FIG. 2) or an anti-TLR3 monoclonal antibody (TLR3.7), and subjected to SDS-PAGE (sodium dodecyl sulfate-polyacrylamide gel electrophoresis) under reducing conditions, followed by immuno-blotting (Western-blotting) with anti-flag monoclonal antibody. Further, anti-TLR2 monoclonal antibody (TLR2.45) was used as a negative-control antibody for immunoprecipitation. An arrowhead of FIG. 2 indicates TLR3 with molecular mass of 116 kDa. A result of the immunoblotting is shown in FIG. 2. As a result, the specificity of the monoclonal antibody TLR3.7 against TLR3 was confirmed also in analysis of immunoprecipitation.

Note that, after a number of trials, the inventors of the present invention established a monoclonal antibody against human TLR3 that recognized the 116 kDa TLR3 protein. The difficulty of screening a monoclonal antibody against human TLR3 was found due to a low expression level of human TLR3 on the murine Ba/F3 cells as shown in FIG. 1(c).

Next, the inventors of the present invention searched for TLR3-positive human cells/cell lines (expressing TLR3 on their surface) by flow cytometry using the monoclonal antibody against various TLRs.

The flow cytometry was performed as follows. Normal human lung fibroblasts MRG-5 and normal human foreskin fibroblasts FS-4 were incubated with the monoclonal antibody (1 µg) against TLR together with human IgG (10 µg) for 30 minutes at 4° C. in FACS (fluorescence activation cell sorter) buffer. Further, the FACS buffer was DPBS (Dulbecco's Phosphoric acid Buffer Solution) containing 0.5% BSA (Bovine Serum Albumin) and 0.1% sodium azide.

After the cells were washed twice with the FACS buffer, FITC (fluorescence isothiocyanate)-labeled secondary antibody (American Qualex) was added and further incubated for 30 minutes at 4° C. The cells were then analyzed on a flow cytometer (FACS Calibur: product of Becton Dickinson). Results thereof are shown in FIG. 3(a), FIG. 3(b), and FIG. 3(c). FIG. 3(a) shows a result of analysis on expression of TLR2 in the cells MRC-5 and FS-4 in accordance with flow cytometry using the monoclonal antibody TLR2.45 against human TLR2. FIG. 3(b) shows a result of analysis on expression of TLR3 in the cells MRC-5 and FS-4 in accordance with flow cytometry using the monoclonal antibody TLR3.75 against human TLR3. FIG. 3(c) shows a result of analysis on expression of TLR4 in the cells MRC-5 and FS-4 in accordance with flow cytometry using the monoclonal antibody HTA125 against human TLR4.

The result of the flow cytometry of FIG. 3(b) shows that TLR3 exists on cell surface of the human lung fibroblasts MRC-5 and the human foreskin fibroblasts FS-4. Thus, it was found that TLR3 is expressed on a cell surface of fibroblasts and inside the fibroblasts (this has not been found until the present study is carried out).

While, as shown in FIG. 3(a) and FIG. 3(c), neither TLR2 nor TLR4 was detected on the cell surface of the human lung fibroblasts MRC-5 and the human foreskin fibroblasts FS-4. These cell lines however expressed the mRNA (messenger RNA) of TLR1, 2, 3, 5, and 6 by RT-PCR (reverse transcription PCR), although their proteins were barely detected by flow cytometry.

Human fibroblasts expressing TLR3 naturally produce interferon-β upon viral infection or stimulation with poly(I):poly(C), a synthetic double-stranded RNA analog. Therefore, as an experiment for inhibiting the interferon-β production on the basis of the double-stranded RNA recognition, the inventors of the present invention examined whether or not the interferon-β production by stimulation of poly(I):poly(C) in the human fibroblasts is inhibited by anti-TLR3 monoclonal antibody.

That is, first, the human lung fibroblasts MRC-5 cells in 24-well plates (7.5×104 cells/wells) were pre-treated with 20 µg/ml of anti-TLR2 monoclonal antibody (TLR2.45: referred to as "Anti-TLR2 mAb" in FIG. 4), or anti-TLR3 monoclonal antibody (TLR3.7: referred to as "Anti-TLR3 mAb" in FIG. 4) for 1 hour at 37° C., then stimulated with polymyxin B-treated poly(I):poly(C) (5 or 10 µg/ml) for 24 hours. The concentrations of interferon-β in the supernatants of the culture media were measured by ELISA (enzyme-linked immuno-sorbent assay) (TFB Inc.). A result of the measurement is shown in FIG. 4.

As apparent from FIG. 4, the pre-treatment of the human lung fibroblasts MRC-5 cells with anti-TLR3 monoclonal antibody inhibited of interferon-β production by poly(I):poly(C), while the human lung fibroblasts treated with anti-TLR2 monoclonal antibody did not. This indicates that TLR3, expressed on the cell surface, participates in the recognition of double-stranded RNA and triggers signaling toward the downstream leading to interferon-β production. The monoclonal antibody resulted in loss of function of TLR3, which is consistent with a previous report (L. Alexopoulou, A. C. Holt, R. Medzhitov, R. A. Flavell: Nature 413 (2001) 732-738) with different approaches. Further, the result offered the possibility of direct blocking of poly(I):poly(C)-mediated interferon-β induction by anti-TLR3 monoclonal antibody.

The foregoing result indicates that the specific recognition of the double-stranded RNA by extracellular TLR3 on the basis of direct or indirect bond between TLR3 and the double-stranded RNA is essential for induction of type I interferon-β. Further, the result also indicates that: the monoclonal antibody bound to the TLR3 inhibits the specific recognition of the double-stranded RNA by the extracellular TLR3, so that the type I interferon production is inhibited.

Thus, it is found that the monoclonal antibody against TLR3 plays a role as an inhibitor for suppressing virus-dependent cellular response occurring via another signaling pathway involving double-stranded RNA-TLR3 recognition which can occur in host cells.

[Verification on Gain-of-Function by Poly(I):Poly(C)]

Fibroblasts produce interferon-β upon viral infection or stimulation by poly(I):poly(C) which is synthesized analog of double-stranded RNA. Therefore, in order to examine the possible role of the TLRs in the recognition of the double-stranded RNA, first, it was confirmed that human fibroblasts induced production of interferon-β upon poly(I):poly(C) stimulation. Specifically, the human lung fibroblasts MRC-5 (cell numbers: 7.5×104) was stimulated with poly(I):poly(C) of various concentrations, ranging from 0 to 20 µg/ml, for 4 or 24 hours. Further, the human foreskin fibroblasts FS-4 (cell numbers: 7.5×104) was stimulated with poly(I):poly(C) of various concentrations, ranging from 0 to 20 µg/ml, for 4 hours. Table 1 shows a result of measurement of amounts of interferon-β produced.

TABLE 1

| Poly(I):poly(C) | Interferon-β (IU/ml) | | |
|---|---|---|---|
| | MRC-5 | | FS-4 |
| (µg/ml) | (4 h) | (24 h) | (4 h) |
| 0 | 0 | 0 | 0 |
| 5 | 9.2 | 15 | 16.5 |

TABLE 1-continued

| Poly(I):poly(C) | Interferon-β (IU/ml) | | FS-4 |
| | MRC-5 | | |
| (µg/ml) | (4 h) | (24 h) | (4 h) |
|---|---|---|---|
| 10 | 13.5 | 24.3 | 27.0 |
| 20 | 16.0 | 42.7 | 43.0 |

As apparent from Table 1, stimulation of the human lung fibroblasts MRC-5 and the human foreskin fibroblasts FS-4 by poly(I):poly(C) induced secretion of interferon-β.

In epithelial cells, poly(I):poly(C) often mimics viral double-stranded RNA to induce activation of NF-κB following secretion of interferon-β and cytokines critical to the host defense against viral infection.

Then, gain-of-function studies were next performed using human cell lines expressing various TLRs so as to examine how TLR3 relates to immune response mechanism in which NF-κB and interferon-β promoter were activated by the recognition of the double-stranded RNA. That is, it was verified whether an immune function was gained or not by poly(I):poly(C) by using human embryonic kidney (HEK) 293 cells expressing various human TLRs transfected with vectors and using a reporter gene assay with the NF-κB and interferon-β.

The reporter gene assay was carried out as follows. First, HEK293 cells (1×106 cells/wells) were transiently transfected in 6-well plates using Lipofectamine 2000 reagent (cationic lipids for gene transfer: product of Gibco, BRL) with human TLR1 expression vector, human TLR2 expression vector, human TLR3 expression vector, human TLR4 expression vector (0.5 or 1 µg), or empty vector, together with a reporter gene.

As the reporter gene, a luciferase-linked NF-κB reporter gene (Stratagene, 0.5 µg) or p-125 luc reporter plasmid (0.5 µg) was used. The p-125 luc reporter plasmid was provided by Dr. Tadatsugu Taniguchi (Graduate School of Medicine and Faculty of Medicine, University of Tokyo) (see T. Taniguchi, K. Ogasawara, A. Takaoka, N. Tanaka, Annu. Rev Immunol. 19 (2001) 623-655). The p-125 luc reporter contains the human interferon-β promoter region (−125 through +19) inserted into the Picagene luciferase reporter plasmid (Toyo Ink). Thus, the p-125 luc reporter plasmid can be used as the interferon-β reporter gene.

The total amount of transfected DNA was kept constant by adding empty vector. Further, the plasmid pCMVβ (Clontech, 0.0025 µg) was used as an internal control.

Twenty-four hours after transfection, cells were harvested, seeded into 24-well plates (2×104/ml), and stimulated with medium alone, lipopolysaccharide (LPS, concentration: 100 ng/ml) from polymixin B, polymixin B-treated mycroplasma lipopeptide, MALP-2 (100 nM), or polymixin B-treated poly (I):poly(C) (50 µg/ml) for 6 hours.

The cells were lysed using lysis buffer (Promega) and both luciferase and β-galactosidase activities were measured according to the manufacturer's instructions.

Table 5 shows a result of measurement in case of using the NF-κB reporter gene as a reporter gene, and Table 6 shows a result of measurement in case of using the interferon-β reporter gene as a reporter gene. Data of Table 5 and Table 6 show average values of relative stimulations.

Figure 5:
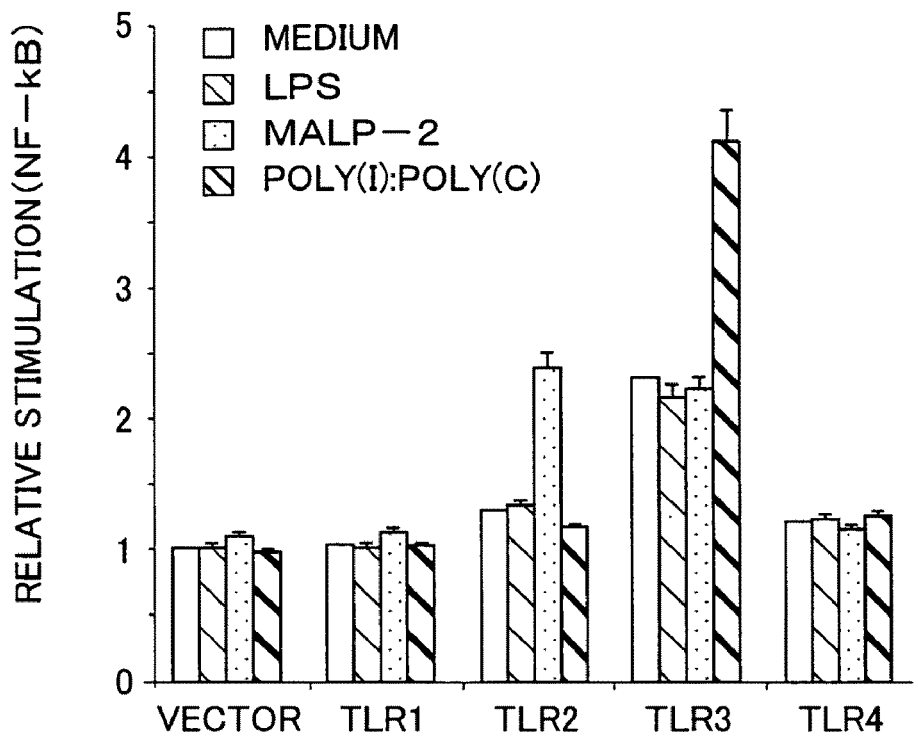
FIG. 5 is a graph showing a result of analysis on whether or not NF-κB is activated by stimulation of poly(I):poly(C) via various TLRs.

HEK293 cells transfected with human TLR3 responded to poly(I):poly(C) so as to activate NF-κB as shown in FIG. 5. While, as shown in FIG. 5, HEK293 cells transfected with other human TLRs (human TLR1, TLR2, and TLR4) did not. However, as shown in FIG. 5, human TLR2-expressing cells responded to mycroplasma lipopeptide, MALP-2, a control TLR2 ligand.

Figure 6:
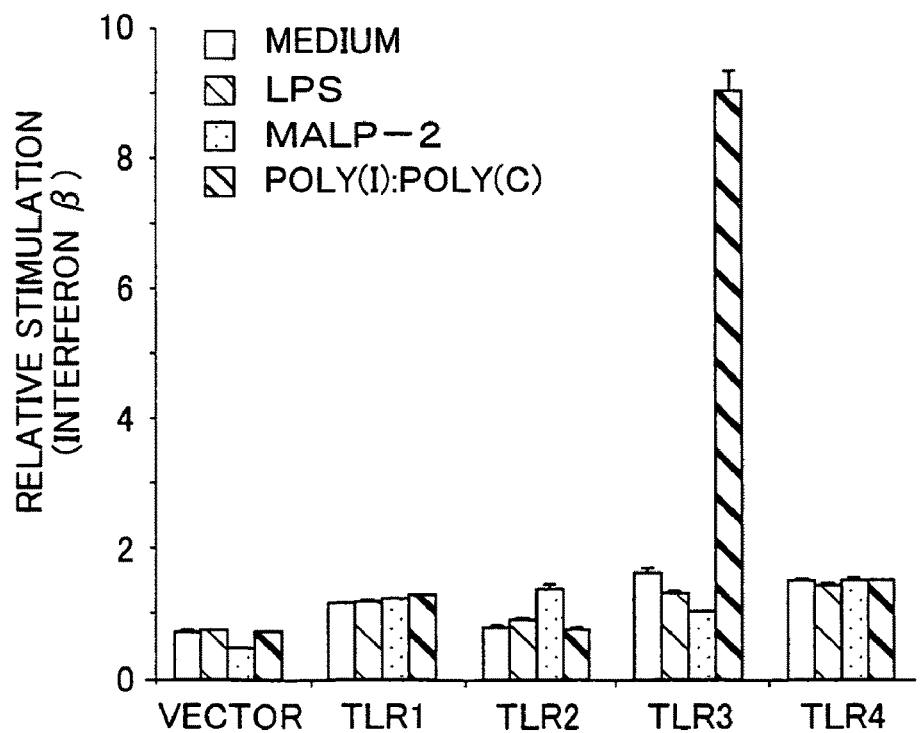
FIG. 6 is a graph showing a result of analysis on whether or not interferon-β promoter is activated by stimulation of poly (I):poly(C) via various TLRs via poly(I):poly(c).

Further, as shown in FIG. 6, human TLR3-expressing cells markedly responded to poly(I):poly(C), and activated interferon-β promoter. Hence, poly(I):poly(C) induced both NF-κB promoter activation and interferon-β promoter activation through TLR3. In contrast, as shown in FIG. 6, cells which express human TLR2 or human TLR4 did not respond to LPS, MALP-2, or poly(I):poly(C), and did not activate interferon-β promoter.

Specificity of poly(I):poly(C) to TLR3 was next examined. First, HEK293 cells were transfected with a reporter gene in the same manner as the foregoing transfection by using human TLR3 expression vector (0.5 or 1 µg) or empty vector. Twenty-four hours after transfection, cells were harvested, seeded into 24-well plates (2×105/ml), and stimulated with medium alone, poly(I):poly(C) (concentration: 50 ng/ml), poly(U), poly(C), poly(dI):poly(dC) (50 µg/ml) for 6 hours.

The cells were lysed using lysis buffer (Promega) and both luciferase and β-galactosidase activities were measured according to the manufacturer's instructions, and evaluated the degree of the activation of luciferase and β-galactosidase promoters.

Figure 7:
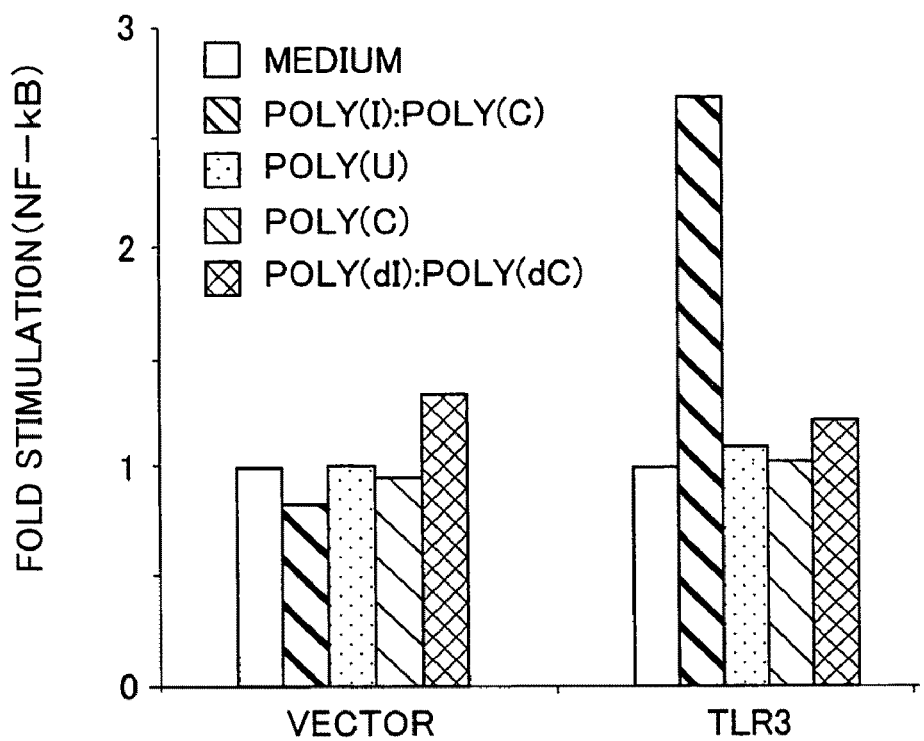
FIG. 7 is a graph showing a result of analysis on whether or not NF-κB is activated by poly(I):poly(c), a single-stranded RNA, and a double-stranded DNA, via the TLR3.
Figure 8:
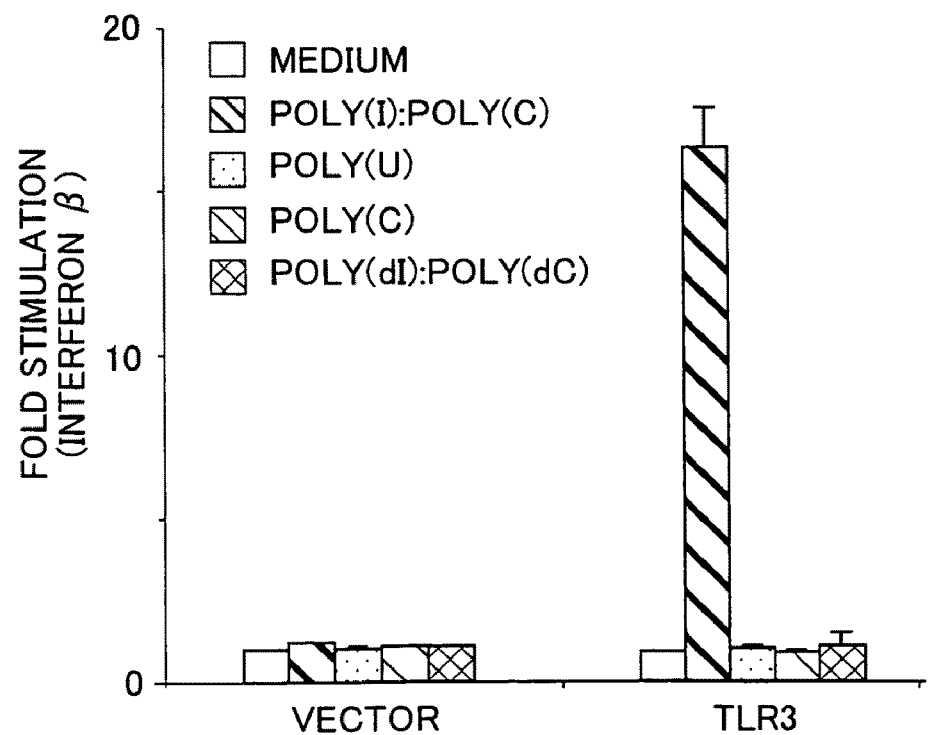
FIG. 8 is a graph showing a result of analysis on whether or not interferon-β promoter is activated by poly(I):poly(c), a single-stranded RNA, and a double-stranded DNA, via the TLR3.

FIG. 7 shows a result of measurement in case of using the NF-κB reporter gene as a reporter gene, and FIG. 8 shows a result of measurement in case of using the interferon-β reporter gene as a reporter gene. Data of FIG. 7 and FIG. 8 are expressed as fold stimulation based on mean plus standard deviation for a representative stimulation experiment from a minimum of three independent experiments.

As shown in FIG. 7 and FIG. 8, TLR3-mediated NF-κB or interferon-β promoter activity was induced by poly(I):poly (C), and TLR3-mediated NF-κB or interferon-β promoter activity was not induced by neither single-stranded RNA (poly(U) or poly(C)) or double-stranded DNA (poly(dI);poly (dC)).

As described above, TLR3 recognized the double-stranded RNA so as to mediate the NF-κB or interferon-β promoter activity by poly(I):poly(C) stimulation, but neither single-stranded RNA nor double-stranded DNA induced the TLR3-mediated signaling.

Thus, it is concluded that TLR3 recognizes very specific structural features in double-stranded RNA, for example, the presence or absence of a hydroxyl group bound to the 2' carbon in β-D-ribose, so that TLR3 selectively recognizes double-stranded RNA, which is unique to viruses, and transmits the signaling from viruses to inside cells.

In this way, the inventors of the present invention found that: TLR3 recognizes double-stranded RNA so as to activate NF-κB and interferon-β promoter, which promotes production of interferon-β. Thus, interferon-β production could be promoted and viral infection could be suppress by promoting the signaling mediated by TLR3. Further, by searching medicaments for promoting the signaling, it would be possible to produce a new inhibitor for viral-infection. Since many of refractory diseases are mediated by viruses, it would be possible to cure such refractory diseases by suppressing viral infection.

Still another object, feature, superior point of the present invention are described as follows. Still another object of the present invention is to apply the foregoing technique to anti-cancer immune therapy (innate immune therapy of cancer) and viral infectious diseases targeting TLR3 (Toll-like receptor 3).

As described above, the inventors of the present invention generated a monoclonal antibody against human Toll-like receptor 3 and found that the antibody specifically inhibits production of double-stranded RNA-mediated interferon-β (IFN-β). Thus, it would be possible to provide a new method for controlling production of virus-dependent IFN-β. It is expected that symptoms of various infectious diseases, cancer (hepatic cancer, cervical cancer, and the like), kidney cancer, and the like induced by viral infection would be improved by a threshold value of IFN-β. In case of cancer, it is known that reduction and/or regression of the cancer could be occurred according to the changing IFN-β sensitivity. Therefore it would be possible to control proliferation of cancerous cells with the antibody of the present invention.

Conventionally, bioregulation mechanisms against bacterial infection have been discussed in terms of "acquired immunity system" mediated by specific T cells and B cells. However, "innate immunity" in host defense (infection control) has come to the front since Toll-like receptor was found several years ago. Double-stranded RNA specifically produced by viral infection activates an immune system (particularly, dendritic cells) via TLR3, so that it has been technically suggested that it is possible to use double-stranded RNA to control immunity upon infection. Main cellular responses against double-stranded RNA are IFN-β production and dendritic cells maturation. However, clinical applications of their effects have not been considered yet.

It would be possible to develop immune therapy for cancer and viral infectious disease by controlling the signaling involving double-stranded RNA-TLR3. Several immune therapies for cancer and viral infectious disease are known: (1) "anticancer immune therapy" developed by using lymph cells (immune therapy with mediation of an acquired immunity system), (2) peptide therapy, and the like. In the technique (1) "anticancer immune therapy", LAK, TIL, adoptive immunity, and the like are used.

However, the technique (1) "anticancer immune therapy" does not necessarily bring about high curing effects. Further, the technique (2) "peptide therapy" does not give high selectivity. Further, the technique (2) "peptide therapy" is effective for melanoma, but is less effective for solid tumor. Further, general treatment effective for viral infection has not been developed yet.

However, when an immune therapy controlling a signaling system of double-stranded RNA-TLR3 is developed by using the present invention, it would be possible to obtain higher selectivity than that of the peptide therapy, and it would be possible to reduce adverse effects. Further, when the immune therapy controlling the signaling involving double-stranded RNA-TLR3 is developed, it would be possible to obtain effects on solid tumors which are partially caused by viruses, such as post-hepatitis C hepatic cancer, cervical cancer, lymphoma, renal cell carcinoma of kidney, and the like.

Further, it was found that ligands for TLR3 (i.e. double-stranded RNA) are produced in virus infection, so that it would be possible to establish a new anti-virus therapy controlling the signaling involving double-stranded RNA-TLR3 by further studying the foregoing mechanism.

When the immune therapy controlling the signaling involving double-stranded RNA-TLR3 is developed, it would be possible to apply the therapy to alleviation of various symptoms induced by double-stranded RNA production due to viral proliferation. Particularly, it would be possible to suppress onset or degeneracy of symptoms that is caused by certain kinds of cancer (kidney cancer, post-hepatitic hepatic cancer) and viral infectious disease (hepatitis B or C virus, measles virus, rotavirus, influenza virus, herpes virus, and the like).

Further, as described above, it is possible to quantitatively analyze expression of TLR3 in cells on the basis of flow cytometry using the antibody of the present invention. Thus, according to the flow cytometry using the antibody of the present invention, it is possible to screen cells expressing TLR3 and to detect cells aberrantly expressing TLR3.

Note that, in analyzing the expression of TLR3 using the antibody of the present invention, it is preferable to adopt the aforementioned method, that is, the method in which: a secondary antibody against anti-TLR3 antibody is labeled with fluorescence so as to measure its fluorescence intensity on the basis of flow cytometry, thereby measuring an antigen antibody reaction between TLR3 and the antibody in cells. However, it is possible to adopt other method. Examples of other method include: a method in which anti-TLR3 antibody is directly labeled with fluorescent so as to measure its fluorescent intensity by flow cytometry; an ELISA method using an enzyme label (enzyme-linked immune adsorption assay); a method in which anti-TLR3 antibody is labeled with radioactive isotopes so as to measure its radioactive intensity; and the like.

The invention being thus described, it will be obvious that the same way may be varied in many ways. Such variations are not to be regarded as a departure from the spirit and scope of the invention, and all such modifications as would be obvious to one skilled in the art are intended to be included within the scope of the following claims.

INDUSTRIAL APPLICABILITY

According to the antibody of the present invention, it is possible to suppress an immune response induced by double-stranded RNA. Thus, the antibody facilitates double-stranded RNA viral infection, and facilitates single-stranded RNA viral infection which has a double-stranded RNA phase during a process of gene replication. Hence, it is possible to improve an transfection efficiency using RNA virus vector such as retrovirus vector without enhancing an infectious capacity of the virus vector, and it is possible to prevent occurrence of excessive immune response. Further, according to the foregoing arrangement, it is possible to suppress immune response selectively, so that it is possible to maintain an immune function of an antigen other than RNA virus, for example, DNA (deoxyribo nucleic acid) viruses or bacteria and the like.

Further, the antibody of the present invention can be used as an auxiliary agent which improves a transfection efficiency in a transfection method or a transfection kit using RNA virus vector.

The invention claimed is:
1. An isolated antibody which binds to human Toll-like receptor 3 and does not bind to human Toll-like receptor 2, wherein said antibody is produced by hybridoma TLR3.7 (FERM BP-10597).

* * * * *